US010426427B2

(12) United States Patent
Dehghan Marvast et al.

(10) Patent No.: US 10,426,427 B2
(45) Date of Patent: Oct. 1, 2019

(54) SYSTEM AND INSTRUMENT FOR DELIVERING AN OBJECT AND METHOD FOR DETECTING DELIVERY

(71) Applicant: KONINKLIJKE PHILIPS N.V., Eindhoven (NL)

(72) Inventors: Ehsan Dehghan Marvast, New York, NY (US); Francois Guy Gerard Marie Vignon, Croton on Hudson, NY (US); Ameet Kumar Jain, New York, NY (US); Shyam Bharat, Arlington, MA (US); Amir Tahmasebi, Cambridge, MA (US); Dirk Binnekamp, Borne (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 577 days.

(21) Appl. No.: 15/102,671

(22) PCT Filed: Dec. 16, 2014

(86) PCT No.: PCT/EP2014/077854
§ 371 (c)(1),
(2) Date: Jun. 8, 2016

(87) PCT Pub. No.: WO2015/091409
PCT Pub. Date: Jun. 25, 2015

(65) Prior Publication Data
US 2016/0302760 A1    Oct. 20, 2016

Related U.S. Application Data

(60) Provisional application No. 61/916,836, filed on Dec. 17, 2013.

(30) Foreign Application Priority Data

Jan. 10, 2014 (EP) ..................................... 14150762

(51) Int. Cl.
A61B 8/00    (2006.01)
A61B 8/08    (2006.01)
(Continued)

(52) U.S. Cl.
CPC .............. *A61B 8/0841* (2013.01); *A61B 8/12* (2013.01); *A61B 8/4483* (2013.01);
(Continued)

(58) Field of Classification Search
CPC ............................................. A61B 2017/3413
See application file for complete search history.

(56) References Cited

U.S. PATENT DOCUMENTS 6,217,518 B1    4/2001  Holdaway et al.
6,447,438 B1    9/2002  Bernardi et al.
(Continued)

FOREIGN PATENT DOCUMENTS

GB    2263641 A       8/1993
WO    2005055849 A1   6/2005

*Primary Examiner* — Omkar A Deodhar

(57) ABSTRACT

The invention relates to a system (10) for providing an object (2) in a body (1), a processor (18) arranged to be used in the system (10) for providing an object (2) in a body (1), an instrument (12) for providing an object (2) into a body (1), a method for detecting a providing of an object (2) in a body (1) and a software product for detecting a providing of an object (2) in a body (1). In order to allow for a providing of an object (2) in a body (1) and a detecting hereof while avoiding the drawbacks on the known approaches, e.g. giving an opportunity for reliable localization in ultrasound images used for real-time monitoring of a medical procedure with reduced error proneness to electromagnetic interference, the invention utilizes the finding that the characteristics of a reception or transmission of an ultrasound transducer (24, 26) are influenced by the surrounding environment of the ultrasound transducer (24, 26). By detecting changes in the characteristics the presence or (Continued)

absence of an object (2) to be provided at the ultrasound transducer (24, 26) is determined.

13 Claims, 5 Drawing Sheets

(51) Int. Cl.
    *A61B 8/12*     (2006.01)
    *A61N 5/10*     (2006.01)
    *A61B 34/20*     (2016.01)
    *A61B 90/00*     (2016.01)

(52) U.S. Cl.
    CPC ............ *A61B 8/4494* (2013.01); *A61B 8/463* (2013.01); *A61B 8/5207* (2013.01); *A61B 34/20* (2016.02); *A61N 5/103* (2013.01); *A61N 5/1007* (2013.01); *A61N 5/1027* (2013.01); *A61N 5/1064* (2013.01); *A61N 5/1071* (2013.01); *A61B 2034/2063* (2016.02); *A61B 2090/392* (2016.02); *A61B 2090/3925* (2016.02)

(56) References Cited

U.S. PATENT DOCUMENTS

| | | |
|---|---|---|
| 7,217,242 B2 | 5/2007 | Alam et al. |
| 9,463,335 B2 | 10/2016 | Griffith et al. |
| 2009/0163804 A1 | 6/2009 | Feleppa et al. |
| 2012/0330088 A1 | 12/2012 | Hillstead et al. |
| 2013/0253387 A1 | 9/2013 | Bonutti et al. |

SYSTEM AND INSTRUMENT FOR DELIVERING AN OBJECT AND METHOD FOR DETECTING DELIVERY

CROSS-REFERENCE TO PRIOR APPLICATIONS

This application is the U.S. National Phase application under 35 U.S.C § 371 of International Application Serial No. PCT/EP2014/077854, filed on Dec. 16, 2013, which claims the benefit of U.S. Application Ser. No. 61/916,836, filed on Dec. 17, 2013 and European Patent Application No 14150762.4, filed on Jan. 10, 2014. These applications are hereby incorporated by reference herein.

FIELD OF THE INVENTION

The invention relates to a system for providing an object in a body, a processor arranged to be used in the system for providing an object in a body, a method for detecting a providing of an object in a body and a software product for detecting a providing of an object in a body.

BACKGROUND OF THE INVENTION

US 2013/0253387 A1 discloses a system for applying vibratory energy to pathologic material in a treatment area of a body. The system comprises an energy source configured to provide an energy signal, a piezoelectric transducer configured to receive the energy signal and an effector operatively coupled to the transducer, wherein the effector has a proximal end connected to a handle and a distal portion configured to apply the vibratory energy to the pathologic material. The system further comprises a cannula having a longitudinal passage to receive at least a portion of the effector and being configured to expose at least the distal portion of the effector to the pathologic material. The transducer is configured to transfer the vibratory energy through the effector to the pathologic material.

Placement of a lattice of radioactive/energy sources inside a cancerous tissue is a form of radiation therapy used for organs such as prostate, lung, breast, head and neck, etc. The position of these sources are preoperatively planned to attain a good coverage of the cancerous tissue with radiation while having a tolerable dose on the surrounding healthy tissue. Source placement errors are common due to factors such as tissue motion and deformation, needle bending, human error, etc.

An example is low-dose-rate (LDR) prostate brachytherapy. LDR prostate brachytherapy entails permanent placement of radioactive seeds inside the prostate to kill the cancer via radiation. The procedure is conventionally performed under transrectal ultrasound (TRUS) guidance. Accurate placement of the seeds leads to better treatment outcome and less toxicity. However, deviations from the plan are inevitable due to problems such as prostate motion and deformation caused by needle insertion, prostate edema, needle bending and human and calibration errors. In current practice, quantitative dosimetry is performed post-operatively using CT images. At this stage, significant deviations from the plan, if detected, should be fixed by repeated treatment which is costly and time consuming.

Accurate localization of the implanted sources with respect to the target anatomy can result in adaptive planning and delivery which can significantly increase the treatment quality. In order to achieve this, the delivered dose to the target and organs/body tissue at risk needs to be measured and monitored in real-time. The treatment plan may then be adapted based on the measured dose to deliver optimal dose coverage.

In many procedures, source placement is performed under real-time ultrasound imaging. In this context, a localization of the sources in the ultrasound coordinate system would allow for a huge improvement in therapy delivery and treatment results. To this end, source localization in ultrasound B-mode images that are used for visual guidance has been tried, so far unsuccessfully. Source localization in ultrasound is hindered by low quality of ultrasound images, shadowing, missing sources and false positives due to calcifications and air bubbles.

Electromagnetic (EM) tracking technology has been suggested to detect the source position at the time of deposition and record the position of needle tip. However, the EM technology is prone to error due to magnetic field interference from a plethora of metallic objects in the operating room. Moreover, the EM coordinate system should be registered to the US coordinate system for dosimetry.

SUMMARY OF THE INVENTION

It is an object of the present invention to allow for a providing of an object in a body and a detecting thereof while avoiding the drawbacks on the known approaches, e.g. giving an opportunity for reliable localization in ultrasound images used for real-time monitoring of a medical procedure with reduced error proneness to electromagnetic interference.

In a first aspect of the present invention a processor arranged to be used in a system for providing an object in a body is presented, wherein the processor is arranged to determine, based on a signal output of one or more ultrasound transducers of an instrument for providing the object in the body which are arranged such that a reception characteristic for receiving an ultrasound transmission from an ultrasound probe changes with a presence of the object to be provided in a portion of the instrument and/or a passing of the object to be provided into and/or from the portion of the instrument, and/or based on a signal output of an ultrasound probe for monitoring an area of the body in which the object is to be provided, the signal output being in response to an ultrasound transmission from one or more ultrasound transducers of the instrument for providing the object in the body which are arranged such that a transmission characteristic for transmitting an ultrasound transmission to the ultrasound probe changes with a presence of the object to be provided in a portion of the instrument and/or a passing of the object to be provided into and/or from the portion of the instrument, whether or not an object to be provided by the instrument is present in the portion of the instrument and/or passing into and/or from the portion of the instrument.

The invention is based on the insight that the characteristics of a reception or transmission of an ultrasound transducer are influenced by the surrounding environment of the ultrasound transducer. In case, for example, of a needle for delivering an object, wherein an ultrasound transducer is provided as a cylinder around a portion of the needle shaft, the acoustic properties of the environment of the transducer are different between a case where an object is present inside the cylinder and a case where no object is present. Disregarding the presence of a fluid medium in the needle, the case of the object being present may be considered as corresponding to the cylinder being filled, while the case of the object being absent may be considered as corresponding to the cylinder being hollow and empty.

The ultrasound probe may be provided on or at the instrument itself, in particular in form of one or more of the ultrasound transducers.

In contrast to the conventional approaches, in this invention it is suggested to use ultrasound-based tracking with ultrasound transducers (preferably at or close to the tip of the instrument, e.g. a needle). The ultrasonically tracked transducers are intrinsically in the US coordinate system and are not sensitive to electromagnetic interference.

This invention can be used, for example in the case of LDR prostate brachytherapy or similar procedures, to localize implanted seeds at the time of deposition and use these positions to calculate real time dosimetry and also update the plan.

In a preferred embodiment, the processor is arranged to determine a position of the instrument relative to the ultrasound probe, based on the signal output of the one or more ultrasound transducers and information on the ultrasound transmission of the ultrasound probe and/or based on information on the ultrasound transmission of the one or more ultrasound transducers and the signal output of the ultrasound probe.

A processing and comparison of the ultrasound transmission and the resulting signal output of the reception may be used for determining a relative position between the transducer(s) of the instrument and the ultrasound probe. At the very least, the timing of transmission and reception gives a distance based on the speed of the ultrasound propagation. If there is a directional aspect to the transmission, this directional aspect may be used for also determining a relative direction between ultrasound probe and ultrasound transducer(s).

In a preferred modification of the above embodiment, the information on the ultrasound transmission consists of or comprises the drive signal for the ultrasound probe or the one or more ultrasound transducers.

The drive signal provides basically quite complete information on the timing and further aspects of the ultrasound transmission. Nevertheless, in addition to or as an alternative to the drive signal other information may also be used. For example, in case of the ultrasound transducers being used for receiving the ultrasound transmission from the ultrasound probe, a further sensor (independent from the ultrasound transducers) may be used for obtaining information on the ultrasound transmission.

In a further aspect of the present invention a system is presented for providing an object in a body, comprising: an ultrasound probe for monitoring an area of the body in which the object is to be provided, an instrument for providing the object in the body, the instrument comprising one or more ultrasound transducers which are arranged such that a reception characteristic for receiving an ultrasound transmission from the ultrasound probe and/or a transmission characteristic for transmitting an ultrasound transmission to the ultrasound probe changes with a presence of the object to be provided in a portion of the instrument and/or a passing of the object to be provided into and/or from the portion of the instrument, a processor arranged to determine, based on a signal output of the one or more ultrasound transducers and/or the ultrasound probe, whether or not an object to be provided by the instrument is present in the portion of the instrument and/or passing into and/or from the portion of the instrument.

In a preferred embodiment, the processor is arranged to determine a position of the instrument relative to the ultrasound probe, based on the signal output of the one or more ultrasound transducers and information on the ultrasound transmission of the ultrasound probe and/or based on information on the ultrasound transmission of the one or more ultrasound transducers and the signal output of the ultrasound probe, wherein the system is arranged for providing multiple objects by delivering the objects to respective positions in the body, further comprising a delivery management unit arranged to store delivery positions of the objects based on the determination of the processor.

The information derived from detecting separate deliveries of objects may be combined into a map of the delivery options in order to obtain an overview of the multiple deliveries.

In a preferred option of the above modification, wherein the delivery management unit is provided with a mapping for positions for the objects to be delivered to and is arranged to modify the mapping for objects to be delivered based on stored delivery positions of delivered objects in order for an overall delivery distribution to conform to a predetermined condition.

A comparison between a predetermined plan for delivering objects and the actual delivery positions of the objects allows for a compensation for deviations between the plan and the actual situation.

In a preferred modification of the above option, the objects to be delivered are radiation sources and the delivery management unit is arranged to compute a radiation dose based on delivery positions of delivered radiation sources and the mapping of radiation sources to be delivered and to modify the mapping for one or more radiation sources to be delivered in case the computed radiation dose does not fall into a predetermined range.

If, for example, a newly calculated projected dose map (based on achieved source positions and the planned positions of the to-be-implanted sources) indicates a possible over-dosing of critical organs or a possible under-dosing of the target, appropriate changes to the planned positions of the to-be-implanted sources may be made.

In a preferred embodiment, the one or more ultrasound transducers are formed to enclose one or more portions of the instrument.

A complete enclosure in the form of, for example, a cylinder arranged around the portion(s) of the instrument, provides the benefit that there is no additional influence of the orientation of the instrument relative to the ultrasound probe, in contrast to a partial enclosure or a provision of the ultrasound transducer(s) just beside the instrument portion.

In a preferred embodiment, at least one of the one or more ultrasound transducers includes a piezoelectric material based on a lead zirconate titanate material, a polyvinlyidene fluoride-trifluoroethylene-copolymer and/or a polyvinlyidene fluoride-tetrafluoroethylene-copolymer, in particular a piezoelectric material obtained by a sol-gel technique and/or a capacitive micromachined ultrasonic transducer and/or a fiber optic hydrophone.

Of the piezomaterials for the ultrasound transducers copolymer-materials and specifically sol-gel solutions are particularly preferred as they provide the advantage that the resulting ultrasound transducers (or sensors) can be made conformable to an object regardless of its curvature. In particular, these materials can be deposited on the outside of a needle or other instrument and the needle (or other instrument) stays smooth; while additionally the lumen of the needle (or other instrument) stays free for delivering objects (e.g. brachytherapy seeds).

In a preferred embodiment, the instrument is arranged for delivering the object into the body through a tip of the instrument, wherein a first one of the one or more ultrasound transducers is arranged at a distance to the tip of the instrument which is less than a length of the object to be delivered, wherein a second one of the one or more ultrasound transducers is arranged at a distance to the first one which is larger than the length of the object to be delivered.

Examples of instruments for delivering an object into a body are needles and (flexible) catheters. Nevertheless other suitable instruments may also be used for implementing the invention.

In a preferred embodiment, the instrument is arranged for removably providing the object at a predetermined position inside the instrument, wherein a first one of the one or more ultrasound transducers is arranged at the position inside the instrument to which the object is to be provided.

The invention is not limited to just delivering an object into a body. Indeed, the invention may also be used, for example, for detecting the positioning of an object (like a radiation source) at the tip of a closed cannula, which is only temporarily to be provided inside the body and may later be removed, either together with the cannula or just from the tip of the cannula.

In a further aspect an instrument for providing an object into a body is presented, the instrument comprising one or more ultrasound transducers which are arranged such that a reception characteristic for receiving an ultrasound transmission from the ultrasound probe and/or a transmission characteristic for transmitting an ultrasound transmission to the ultrasound probe changes with a presence of the object to be provided in a portion of the instrument and/or a passing of the object to be provided into and/or from the portion of the instrument, wherein the ultrasound transducers are arranged either just for reception or just for transmission.

In the context of the system for providing an object in a body, the one or more transducers of the instrument for providing the object are not necessarily arranged either just for reception or just for transmission. In particular, in embodiments having one or more further features of the embodiments of the instrument as discussed below, the one or more transducers may also be arranged for both, transmission and reception.

Furthermore, it is to be understood that in case of multiple transducers, some of these transducers might be arranged for just reception while other transducers might be arranged for just transmission such that the plurality of transducers in total may be arranged for both, transmission and reception, A method for detecting a providing of an object in a body, comprising a combination of the steps of providing ultrasound transmission by an ultrasound probe, and receiving a signal output of one or more ultrasound transducers of an instrument for providing the object in the body which are arranged such that a reception characteristic for receiving the ultrasound transmission changes with a presence of the object to be provided in a portion of the instrument and/or a passing of the object to be provided into and/or from the portion of the instrument, and/or a combination of the steps of providing ultrasound transmission by one or more ultrasound transducers of an instrument for providing the object in the body which are arranged such that a transmission characteristic for transmitting the ultrasound transmission changes with a presence of the object to be provided in a portion of the instrument and/or a passing of the object to be provided into and/or from the portion of the instrument, and receiving a signal output of an ultrasound probe for monitoring an area of the body in which the object is to be provided in response to the ultrasound transmission, further comprising processing the received signal output using information on the ultrasound transmission and detecting the providing of the object in the body based on the processing.

In a further aspect of the present invention a computer program is presented for detecting a providing of an object in a body, the software product comprising program code means for causing a processor according to the invention to carry out the steps of the method for detecting according to the invention when the software product is run on the processor.

It shall be understood that the processor system instrument, method, and the computer program described herein have similar and/or identical preferred embodiments .

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
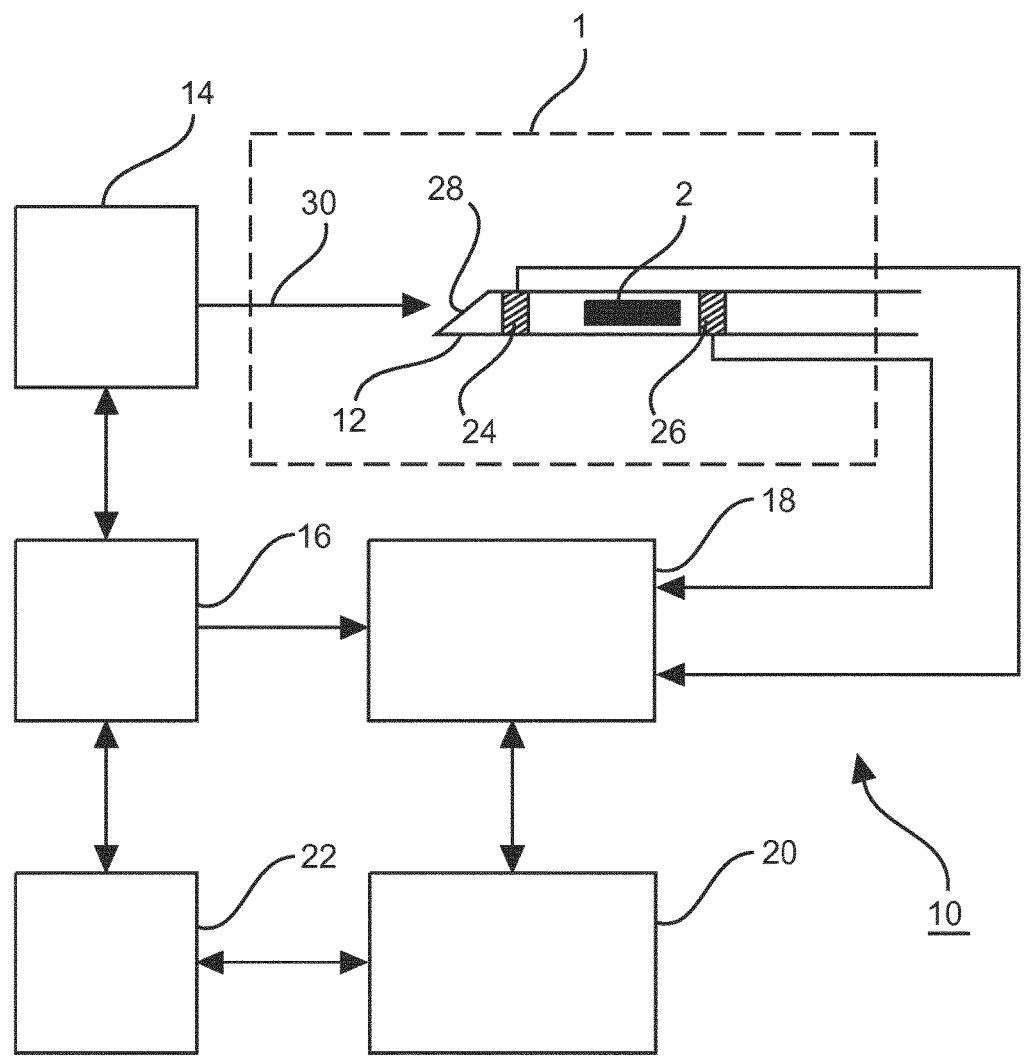
FIG. 1 shows a schematic illustration of a system for providing an object in a body in accordance with an embodiment of the invention.

FIG. 1 shows a schematic illustration of a system 10 for providing an object 2 in a body 1 in accordance with an embodiment of the invention.

The system 10 includes a needle 12 as the instrument for delivering the object 2 into the body 1, an ultrasound probe 14, a control unit 16 for the ultrasound probe 14, a processor 18 coupled to the control unit 16, a delivery management unit 20 coupled to the processor 18 and an interface 22 for interacting with a user of the system 10.

The object 2 is a radioactive source used for brachytherapy of the body 1.

The needle 12 is hollow for allowing the delivery of the object 2 into the body and is provided with two ultrasound transducers 24, 26, wherein one ultrasound transducer 24 is arranged close to a tip 28 of the needle 12 through which the object 2 is released into the body 1, while the other ultrasound transducer 26 is arranged distant to the one ultrasound transducer 24 opposite to the tip 28. As schematically shown in FIG. 1, the needle 12 is inserted into the body 1.

The ultrasound probe 14 is provided for monitoring the area of the body 1 into which the object 2 is to be delivered and provides ultrasound transmissions (indicated by arrow 30) in response to a drive signal provided by the control unit 16. The ultrasound probe 14 receives reflections of the ultrasound transmission from the interior of the body 1 and provides data for an ultrasound image to the control unit 16.

The ultrasound transmission 30 is received by the ultrasound transducers 24 and 26, wherein the corresponding signal output of the ultrasound transducers 24 and 26 is provided to the processor 18.

The processor 18 further receives from the control unit 16 the drive signal provided to the ultrasound probe 14. Using the drive signal and the signal output of the ultrasound transducers 24 and 26, the processor is able to determine a position of the needle 12 in relation to the ultrasound probe 14. A direction from the ultrasound probe 14 can be found by identifying the beam from the ultrasound probe 14 that delivers the strongest wave to the respective ultrasound transducer 24, 26, using the timing and information on the beam firing sequence of the ultrasound probe 14. The distance of the ultrasound transducer 24, 26 from the ultrasound probe 14 is calculated using the time of flight of the transmission.

Furthermore, the processor 18 is arranged for detecting a change in the signal output of either of the ultrasound transducers 24 and 26 indicative of a change of the acoustic properties or characteristics of the surrounding of the respective ultrasound transducer 24, 26.

Based on such detection, the processor 18 is arranged for detecting a delivery of an object 2 from the needle 12 into the body 1, wherein the processor 18 forwards information on such detection to the delivery management unit 20.

The delivery management unit 20 stores the positions of already delivered objects and is provided with a predetermined plan for delivery positions according to a desired brachytherapy treatment. The delivery management unit 20 determines an estimated dose for a cancerous area and surrounding tissue (not shown) in the body 1 and compares the determined estimating with a range considered allowable according to the treatment plan. In order to compensate for a deviation from the plan, the delivery management unit 20 either suggests or implements a change in the delivery positions of objects yet to be delivered. The delivery management unit 20 and the control unit 16 of the ultrasound probe 14 are coupled to the interface 22 for providing information to the user and for receiving instructions from the user.

Figure 2:
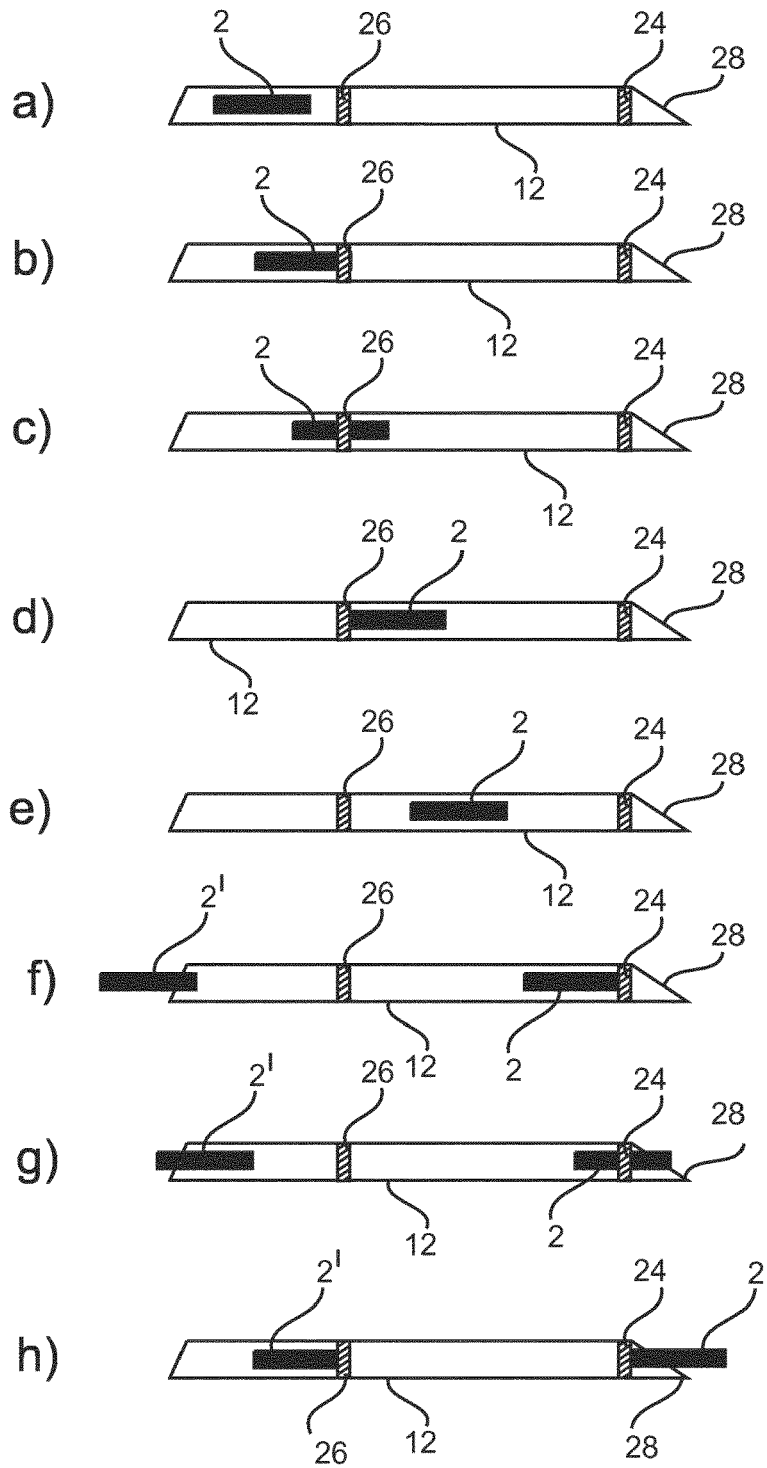
FIG. 2 shows several situations during the delivery of an object through an instrument for providing an object into a body corresponding to the embodiment shown in FIG. 1.

FIG. 2 shows several situations during the delivery of an object 2, 2' through an instrument 12 for providing an object 2, 2' into a body corresponding to the embodiment shown in FIG. 1.

As indicated above, the instrument 12 is a hollow needle 12, wherein at two different positions ultrasound transducers 24, 26 are provided, which allow for a detecting of an object 2, 2' passing through the transducers 24, 26. The transducers 24, 26 are provided as cylinders respectively surrounding portions of the interior of the needle 12.

In FIG. 2a) the object 2 to be delivered has not yet reached either of the ultrasound transducers 24, 26 and therefore none of the ultrasound transducers 24, 26 may indicate the presence of the object 2 in the respective portion of the needle 12.

In FIG. 2b) the object 2 has just reached the portion of the needle 12 surrounded by ultrasound transducer 26. Accordingly, the signal output of the ultrasound transducer 26 is affected by the presence of the object 2, while the signal output of the ultrasound transducer 24 is not influenced.

In FIGS. 2c) and 2d) the object 2 has further progressed through the needle 12 but is still at least partially in the region surrounded by ultrasound transducer 26. Accordingly, the signal outputs of the ultrasound transducers 24, 26 correspond to those of FIG. 2b).

In FIG. 2e) the object 2 has left the region surrounded by ultrasound transducer 26 and has not yet reached the region of the ultrasound transducer 24. Accordingly, the signal outputs of the ultrasound transducers 24, 26 correspond to those of FIG. 2a).

In FIG. 2f) the object 2 has reached the region of influence to ultrasound transducer 24, affecting the signal output of the ultrasound transducer 24. A further object 2' is provided in the needle 12 but has not yet arrived at the ultrasound transducer 26.

In FIG. 2g) the object 2 partially passed through the portion of the needle 12 enclosed by the ultrasound transducer 24, thus still influencing the signal output of the ultrasound transducer 24 due to the object's impact on the acoustic characteristics. The further object 2' has not yet reached the other ultrasound transducer 26.

In FIG. 2g) the object 2 has passed the ultrasound transducer 24 and is about to be delivered by the needle 12 into the body (not shown). The further object 2' has now reached the ultrasound transducer 26 and is therefore also detectable in the area close to the tip 28 of the needle 12.

Figure 3:
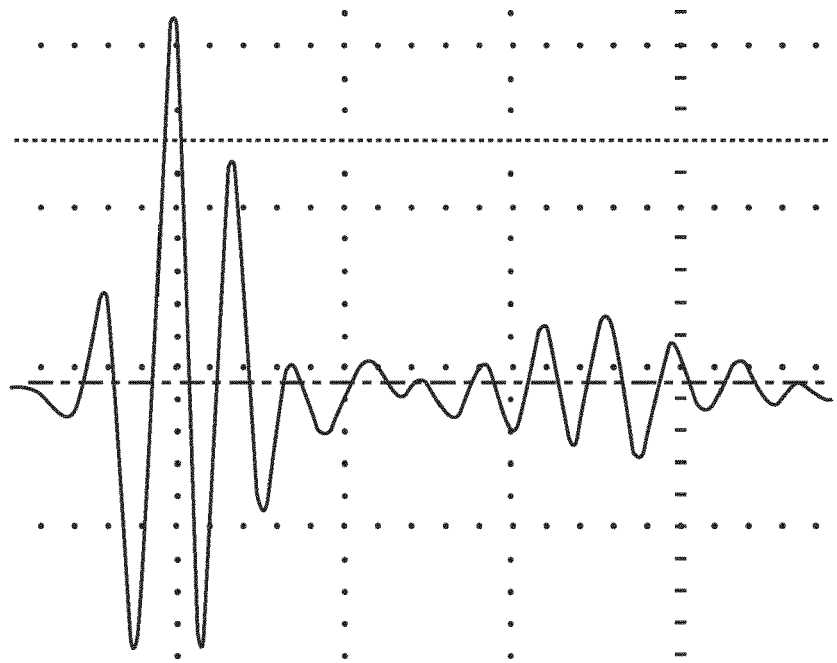
FIG. 3 shows an exemplary waveform of a signal output of an ultrasound transducer with no object being present.
Figure 4:
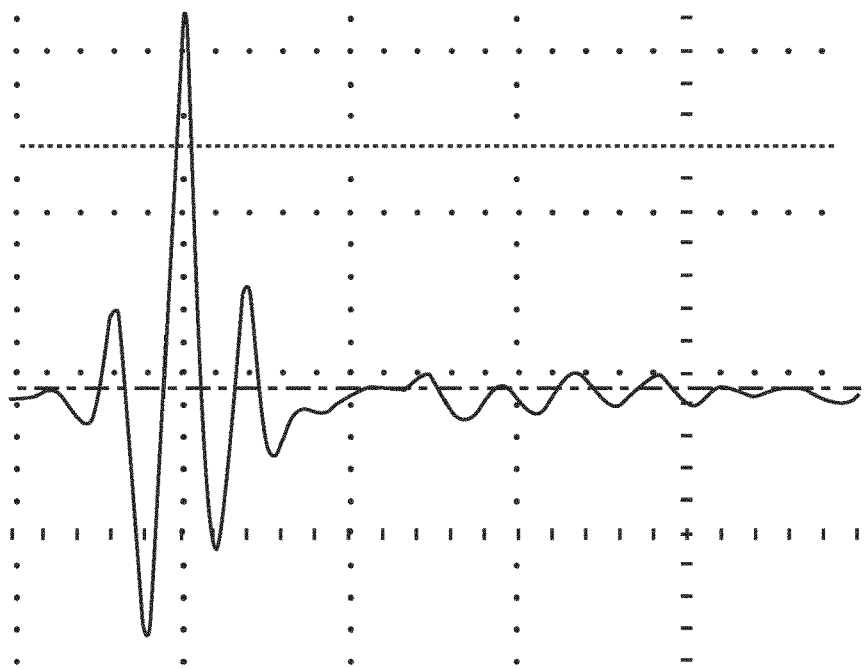
FIG. 4 shows an exemplary waveform of a signal output of an ultrasound transducer with an object being present.

FIG. 3 shows an exemplary waveform of a signal output of an ultrasound transducer with no object being present, wherein FIG. 4 shows an exemplary waveform of a signal output of an ultrasound transducer with an object being present.

As a proof-of-concept experiment, an 18-gage stainless steel needle was equipped with a cylindrical copolymer sensor near its tip that allows tracking of the needle at depths >15 cm in ex-vivo tissue. The changes in acoustic signal were recorded as an inner stylet is removed and then introduced in the lumen (mimicking a source passing through). The results of these recordings are shown schematically in FIG. 3 and FIG. 4. The reverberations in the signal waveform are mostly due to the changes in the acoustical backing material to the needle. As seen in FIG. 4, with a perfect impedance match (stylet in, between the steel of the outer needle shaft and that of the stylet) there are few reverberations. In contrast, as shown in FIG. 3, with a large impedance mismatch (here, between the steel of the needle and water in the lumen) a reverberation can be seen (right part of FIG. 3). With, for example, a radioactive/energy source passing through, a reduction in reverberation will occur and this can be detected through known change detection methods, e.g. cross-correlations or sum of absolute differences of successively received waveforms.

Figure 5:
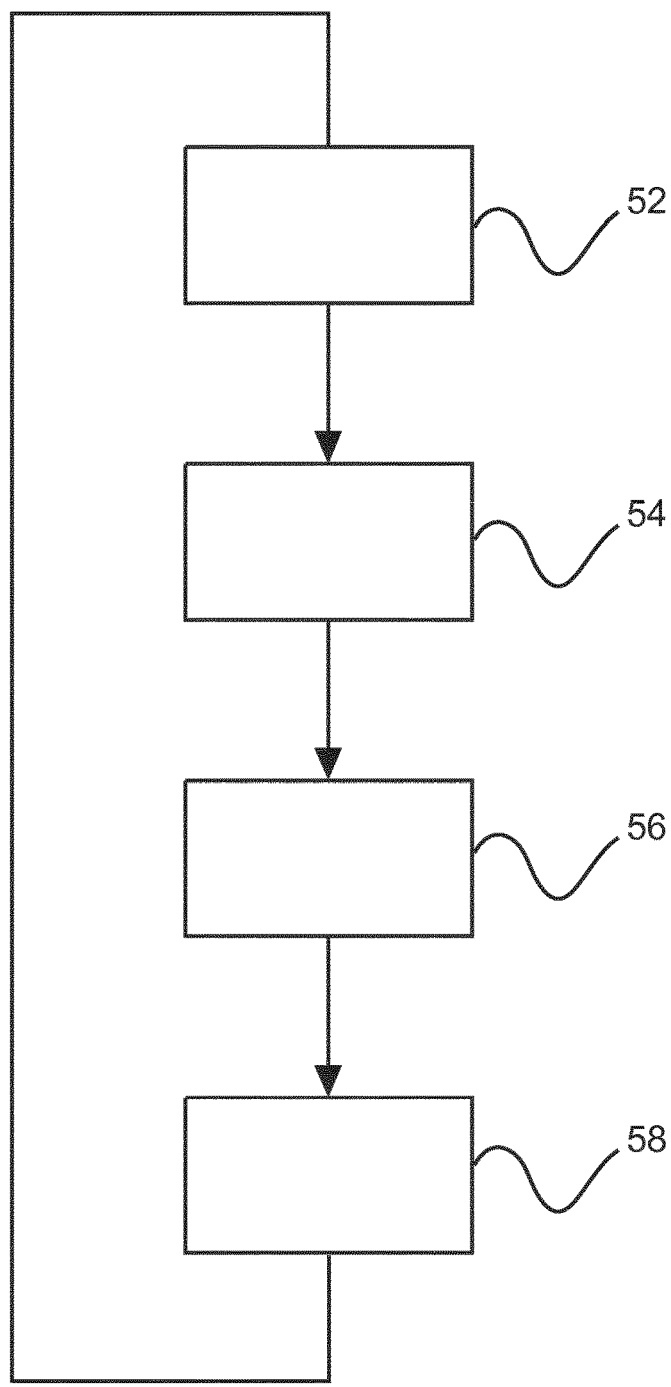
FIG. 5 shows a schematic flow diagram of a method for detecting a providing of an object in a body according to an embodiment of the invention.

FIG. 5 shows a schematic flow diagram of a method for detecting a providing of an object in a body according to an embodiment of the invention.

The method includes a providing 52 of ultrasound transmission by an ultrasound probe (see FIG. 1). The ultrasound transmission is received by the one or more ultrasound transducers provided at the instrument for providing the object in the body.

The ultrasound transducers (see FIG. 1) are arranged such that a reception characteristic in receiving the ultrasound transmission changes with a presence of the object to be provided in a portion of the instrument and/or a passing of the object to be provided into and/or from the portion of the instrument. There is a reception 54 of resulting signal output, followed by a processing 56 of the received signal output using information on the ultrasound transmission and a detecting 58 of the providing of the object in the body based on the processing, in case the object due to its presence influences the acoustic properties of the ultrasound transducers or their surroundings.

Figure 6:
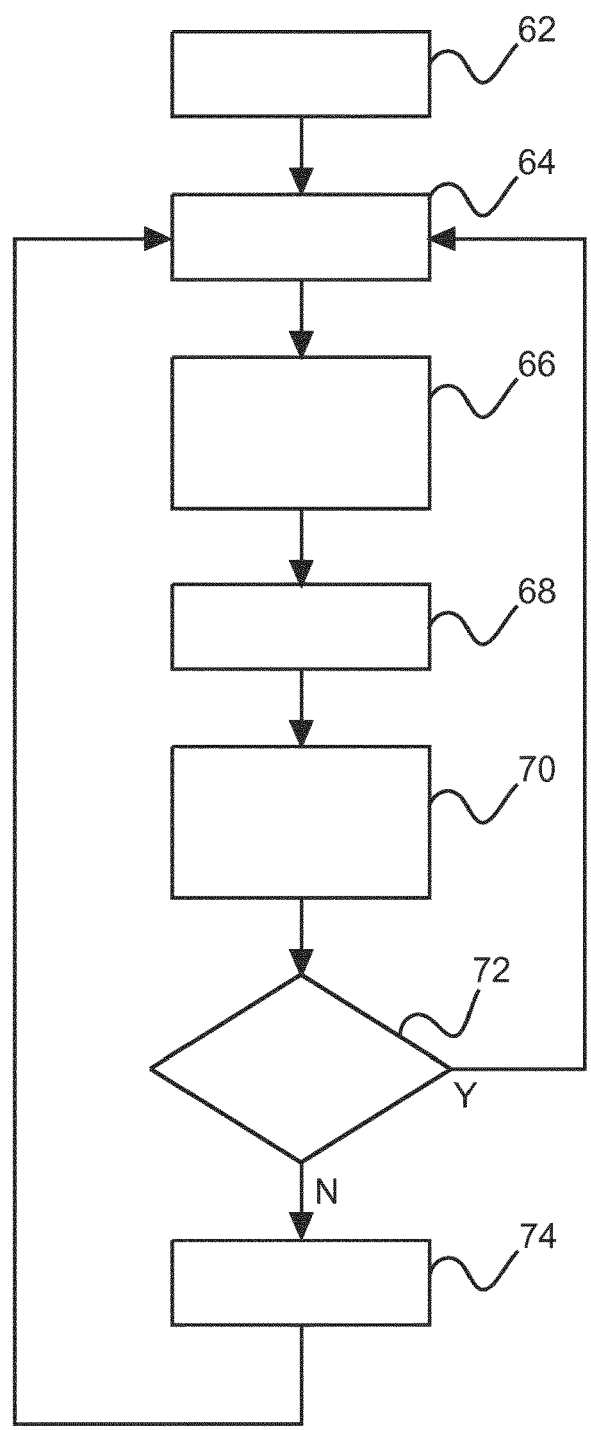
FIG. 6 shows a schematic flow diagram illustrating an adaptive planning of delivering of objects into a body according to a further embodiment of the invention.

FIG. 6 shows a schematic flow diagram illustrating an adaptive planning of delivering of objects into a body according to a further embodiment of the invention.

In a creation step 62, a plan for brachytherapy is created, including a map for the positions of radiation sources to be delivered to.

In a drop step 64, a radiation source is dropped or positioned inside the body of the patient.

In a localization step 66, the dropping or delivery position of the radiation source is determined according to the present invention (see above).

In a dose computing step 68, based on the determined positions of delivered radiation sources and the delivery positions for the further radiation sources as defined in the plan, the delivered dose is computed.

In a display step 70, the computed dose is overlaid on an ultrasound image for determination by the user of whether or not the dose is adequate. Alternatively, the adequacy of the dose may be determined automatically based on predetermined ranges or values.

In branching step 72, the process branches depending on the result of the adequacy determination. If the dose is OK, the process is brought to the drop step 64 (as long as further radiation sources are to be delivered). If the dose is not OK, in a modification step 74, the plan is modified, either automatically or in accordance to a user input, wherein after the modification step 74 the process is continued in the drop 64 (as long as further radiation sources are to be delivered).

In an exemplary embodiment of the invention, there are provided adaptive planning and therapy delivery entailing localization of the already implanted sources and modification of the planned position and number of the remaining sources to cover up the under-radiated regions and avoid over-radiating the organs at risk.

In order to get an estimation of source positions, the needle used for delivery is equipped with at least one special sensor such as PZT or copolymer (PVDF-trFE) sensor to track the needle and detect the source drop time and position. These sensors are embedded inside each needle at the time of manufacturing. A source passing through the sensor changes the acoustic properties of the sensor and hence changes the output signal of the sensor. This change can be detected by a processing unit so that the time of source deposition can be detected. As the sensors provide needle tip position at real-time, the source deposition position can be calculated as the needle tip position at the time of deposition.

The elements of this exemplary embodiment include a hollow needle equipped with one or more ultrasound sensors, a 3D/2D ultrasound probe (transrectal, in case of prostate brachytherapy) to image the tissue, a hardware module to receive and interpret the signal from the sensors, a software module to detect the time and position of the deposited sources, a user interface to display the real-time position of implanted sources and the corresponding radiation dose map overlaid on the real-time ultrasound image and a software module to measure the delivered dose to the target and the organs at risk and update the treatment plan.

As indicated above, the needle (being the instrument for providing the object in this embodiment) is equipped with one or more cylindrical single-element US transducer sensors such as PZT or copolymer (PVDF-trFE), at or very near the tip of the needle. The ultrasound tracking technology can estimate the position of the sensor by analyzing the radio-frequency (RF) signal received by the sensor from the ultrasound probe. The hydrophone is localized, first, by identifying the beam from the ultrasound array that delivers the strongest wave to the sensor. This is performed using the knowledge of the beam firing sequence. The distance of the sensor from the corresponding ultrasound element is calculated using the time of flight. The position of the sensors can thus be determined in real-time.

The signal output of the ultrasound sensor depends on its acoustic properties. When a source passes through the hollow needle with the cylindrical sensor, it changes the acoustic properties of the sensor and hence the output signals (magnitude, phase, waveform) of the sensor.

The computer software module can detect the change in the output of the sensor and hence detect the time that the seed passed through the sensor and subsequently the position of the seed when it was dropped.

The information from a sensor is transferred to a central computer for processing. The output of the processing algorithm is the coordinates of each radioactive source in the coordinate system of the imaging US probe. The estimated source locations may be highlighted on the images (using crosses, or other suitable indicators) in one of two ways: The real-time US images may be read into the processing workstation and the estimated source positions may be superimposed in real-time on the appropriate locations in the incoming images or the estimated source positions may be transferred to the US system for display on the US system screen.

The adaptive planning using estimated source locations includes that the position estimates of the sources are utilized to continuously re-compute the dose based on achieved source positions. If the new projected dose map (based on achieved source positions and the planned positions of the to-be-implanted sources) indicates over-dosing of critical organs or under-dosing of the target, appropriate changes to the planned positions of the to-be-implanted sources may be made.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

For example, it is possible to operate the invention in an embodiment wherein the transmission of the ultrasound signal is provided by the ultrasound transducers provided on the instrument for providing the object in the body, wherein the transmitted ultrasound signal (indicative of the presence or absence of the object in the portion of interest of the instrument) is then either received by the ultrasound transducers of the instrument themselves (due to reflections and the like inside the body) or by the ultrasound probe. It is also possible to combine these aspects, i.e. to provide transmissions from both, the ultrasound probe and the ultrasound transducer(s), and reception by both, the ultrasound transducer(s) and the ultrasound probe.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like providing ultrasound transmissions, receiving signal outputs, processing the signal output(s) and detecting the providing of the object can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for providing an object in a body, comprising:
an ultrasound probe for monitoring an area of the body in which the object is to be provided;
an instrument for providing the object in the body, the instrument comprising one or more ultrasound transducers which are arranged such that a reception characteristic for receiving an ultrasound transmission from the ultrasound probe and/or a transmission characteristic for transmitting an ultrasound transmission to the ultrasound probe changes with a presence of the object to be provided in a portion of the instrument and/or a passing of the object to be provided into and/or from the portion of the instrument; and
a processor arranged to be used in a system for providing an object in a body, wherein the processor is arranged to determine, based on a signal output of one or more ultrasound transducers of an instrument for providing the object in the body which are arranged such that a reception characteristic for receiving an ultrasound transmission from an ultrasound probe changes with a presence of the object to be provided in a portion of the instrument or a passing of the object to be provided into or from the portion of the instrument, or based on a signal output of an ultrasound probe for monitoring an area of the body in which the object is to be provided, the signal output being in response to an ultrasound transmission from one or more ultrasound transducers of the instrument for providing the object in the body which are arranged such that a transmission characteristic for transmitting an ultrasound transmission to the ultrasound probe changes with a presence of the object to be provided in a portion of the instrument or a passing of the object to be provided into or from the portion of the instrument, without regard to an object to be provided by the instrument being present in the portion of the instrument or passing into or from the portion of the instrument,
wherein; the processor is arranged to determine, based on a signal output of the one or more ultrasound transducers or the ultrasound probe, if, at least, an object to be provided by the instrument is present in the portion of the instrument or passing into or from the portion of the instrument; and to determine a position of the instrument relative to the ultrasound probe based on the signal output of the one or more ultrasound transducers and information on the ultrasound transmission of the ultrasound probe, or based on information on the ultrasound transmission of the one or more ultrasound transducers and the signal output of the ultrasound probe, wherein the system is arranged for providing multiple objects by delivering the objects to respective positions in the body, further comprising a delivery management circuit arranged to store delivery positions of the objects based on the determination of the processor.

2. The system according to claim 1 wherein the delivery management circuit is provided with a mapping for positions for the objects to be delivered to and is arranged to modify the mapping for objects to be delivered based on stored delivery positions of delivered objects in order for an overall delivery distribution to conform to a predetermined condition.

3. The system according to claim 2, wherein the objects to be delivered are radiation sources and the delivery management circuit is arranged to compute a radiation dose based on delivery positions of delivered radiation sources and the mapping of radiation sources to be delivered and to modify the mapping for one or more radiation sources to be delivered in case the computed radiation dose does not fall into a predetermined range.

4. The system according to claim 1, wherein the one or more ultrasound transducers are formed to enclose one or more portions of the instrument.

5. The system according to claim 1, wherein at least one of the one or more ultrasound transducers includes a piezoelectric material based on a lead zirconate titanate material, a polyvinlyidene fluoride-trifluoroethylene-copolymer or a polyvinlyidene fluoride-tetrafluoroethylene-copolymer, in particular a piezoelectric material obtained by a sol-gel technique or a capacitive micromachined ultrasonic transducer or a fiber optic hydrophone.

6. The system according to claim 1, wherein the instrument is arranged for removably providing the object at a predetermined position inside the instrument, wherein a first one of the one or more ultrasound transducers is arranged at the position inside the instrument to which the object is to be provided.

7. A system for providing an object in a body, wherein the object is a radiation source for radiation therapy and the system comprises:
an ultrasound probe for monitoring an area of the body in which the object is to be provided;
an instrument for providing the object in the body , the instrument comprising one or more ultrasound transducers, which are arranged such that a reception characteristic for receiving an ultrasound transmission from the ultrasound probe or a transmission characteristic for transmitting an ultrasound transmission to the ultrasound probe changes with a presence of the object to be provided in a portion of the instrument or a passing of the object to be provided into or from the portion of the instrument; and
a processor arranged to determine, based on a signal output of one or more ultrasound transducers of an instrument for providing the object in the body, which are arranged such that a reception characteristic for receiving an ultrasound transmission from an ultrasound probe for monitoring an area of the body, in which the object is to be provided, changes with a presence of the object to be provided in a portion of the instrument or a passing of the object to be provided into or from the portion of the instrument, or based on the signal output of an ultrasound probe for monitoring an area of the body in which the object is to be provided, the signal output being in response to an ultrasound transmission from one or more ultrasound transducers of the instrument for providing the object in the body, the one or more ultrasonics transducer being arranged such that a transmission characteristic for transmitting an ultrasound transmission to the ultrasound probe changes with a presence of the object to be provided in a portion of the instrument and/or a passing of the object to be provided into and/or from the portion of the instrument, without regard to an object to be provided by the instrument being present in the portion of the instrument or passing into or from the portion of the instrument, wherein: the instrument is arranged for delivering the object into the body through a tip of the instrument; a first one of the one or more ultrasound transducers is arranged at a distance to the tip of the instrument, the distance being less than a length of the object to be delivered; and a second one of the one or more ultrasound transducers is arranged at a distance to the first one which is larger than the length of the object to be delivered.

8. The system according to claim 7, wherein the processor is arranged to determine a position of the instrument relative to the ultrasound probe, based on the signal output of the one or more ultrasound transducers and information on the ultrasound transmission of the ultrasound probe and/or based on information on the ultrasound transmission of the one or more ultrasound transducers and the signal output of the ultrasound probe, wherein the system is arranged for providing multiple objects by delivering the objects to respective positions in the body, further comprising a delivery management circuit arranged to store delivery positions of the objects based on the determination of the processor.

9. The system according to claim 8, wherein the delivery management circuit is provided with a mapping for positions for the objects to be delivered to and is arranged to modify the mapping for objects to be delivered based on stored delivery positions of delivered objects in order for an overall delivery distribution to conform to a predetermined condition.

10. The system according to claim 9, wherein the objects to be delivered are radiation sources and the delivery management circuit is arranged to compute a radiation dose based on delivery positions of delivered radiation sources and the mapping of radiation sources to be delivered and to modify the mapping for one or more radiation sources to be delivered in case the computed radiation dose does not fall into a predetermined range.

11. The system according to claim 7, wherein the one or more ultrasound transducers are disposed to enclose one or more portions of the instrument.

12. The system according to claim 7, wherein at least one of the one or more ultrasound transducers includes a piezoelectric material based on a lead zirconate titanate material, a polyvinlyidene fluoride-trifluoroethylene-copolymer or a polyvinlyidene fluoride-tetrafluoroethylene-copolymer, in particular a piezoelectric material obtained by a sol-gel technique or a capacitive micromachined ultrasonic transducer or a fiber optic hydrophone.

13. The system according to claim 7, wherein the instrument is arranged for removably providing the object at a predetermined position inside the instrument, wherein a first one of the one or more ultrasound transducers is arranged at the position inside the instrument to which the object is to be provided.

* * * * *